United States Patent
Evans et al.

[11] Patent Number: 5,900,190
[45] Date of Patent: May 4, 1999

[54] POLYFLUOROALKYL SILOXANES

[75] Inventors: Edwin R. Evans; David C. Gross, both of Clifton Park, N.Y.

[73] Assignee: General Electric Company, Waterford, N.Y.

[21] Appl. No.: 09/115,437

[22] Filed: Jul. 15, 1998

Related U.S. Application Data

[62] Division of application No. 08/940,794, Sep. 30, 1997, Pat. No. 5,834,578.

[51] Int. Cl.$^6$ ...................................................... H01B 1/06
[52] U.S. Cl. ........................... 252/511; 523/218; 523/219; 524/430; 524/432; 524/450; 524/588; 528/36
[58] Field of Search ...................................... 524/588, 432, 524/430, 450; 252/511; 528/36; 523/218, 219

[56] References Cited

U.S. PATENT DOCUMENTS

| | | |
|---|---|---|
| 3,967,042 | 6/1976 | Laskin et al. . |
| 4,537,677 | 8/1985 | Keil . |
| 4,812,251 | 3/1989 | Stangroom . |
| 5,389,497 | 2/1995 | Yoshioka et al. . |
| 5,391,314 | 2/1995 | Mineumura et al. . |
| 5,427,706 | 6/1995 | Kobayashi et al. . |
| 5,480,573 | 1/1996 | Durfee et al. . |
| 5,489,328 | 2/1996 | Ono et al. . |
| 5,503,763 | 4/1996 | Podszun et al. . |
| 5,547,049 | 8/1996 | Weiss et al. . |
| 5,558,803 | 9/1996 | Okada et al. . |
| 5,558,811 | 9/1996 | Pialet . |
| 5,578,238 | 11/1996 | Weiss et al. . |
| 5,595,680 | 1/1997 | Bryant et al. . |
| 5,607,617 | 3/1997 | Inoue et al. . |

*Primary Examiner*—Morton Foelak
*Attorney, Agent, or Firm*—Kenneth S. Wheelock

[57] ABSTRACT

A polyfluoroalkyl silicone having the general formula:

$$M_a M'_b D_c D'_d T_e T'_f Q_g;$$

where $M = R^1_u R^2_v R^3_w SiO_{1/2}$ with the sum of the subscripts u+v+w being 3 and the subscripts v and w are each independently 0 or 1;

$M' = R^4 R^5 R^6 SiO_{1/2}$;

$D = R^7_x R^8_y SiO_{2/2}$ with the sum of the subscripts x+y being 2 and y is 0 or 1;

$D' = R^9 R^{10} SiO_{2/2}$;

$T = R^{11}_z SiO_{3/2}$ with the subscript z being 1;

$T' = R^{12} SiO_{3/2}$; and $Q = SiO_{4/2}$;

where the substituent groups $R^2, R^3, R^4, R^5, R^6, R^8, R^9, R^{10}$, and $R^{12}$ are each independently selected from the group of one to forty carbon atom monovalent hydrocarbon radicals, the subscripts a, b, c, d, e, f, and g are zero or positive integers with the substituent groups, $R^1$, $R^7$, and $R^{11}$, each independently selected from the group of consisting of monovalent polyfluoroalkyl groups having the formula $CF_3(CF_2)_n(CH_2)_m$ and monovalent polyfluoroalkyl groups having the formula $CF_3(CF_2)_n J(CH_2)_m$ where the subscript n is an integer that ranges from about 3 to about 20, the subscript m is an integer that ranges from about 2 to about 20, J is a divalent methylene group ($CH_2$), divalent sulfur (S), or oxygen (O); subject to the following limitations on the stoichiometric subscripts a, b, c, and e:

1) $a+b \geq 2$;

2) $a+c+e \geq 1$; and $a(u)+c(x)+e(z) \geq 2$ as a carrier fluid for electro-active materials thereby providing for an electro-viscous fluid.

17 Claims, No Drawings

POLYFLUOROALKYL SILOXANES

This is a divisional of co-pending application Ser. No. 08/940,794 filed on Sep. 30, 1997 now U.S. Pat. No. 5,834,578.

FIELD OF THE INVENTION

The present invention relates to siloxanes substituted by polyfluoroalkyl groups. More particularly the present invention relates to low molecular weight siloxanes substituted by polyfluoroalkyl groups which are particularly well suited for electro-rheological applications. The polyfluoroalkyl siloxanes of the present invention may be monomers, dimers, trimers, oligomers and homo- or co-polymers and may be linear or branched.

BACKGROUND OF THE INVENTION

Electro-rheological or electro-viscous fluids are dispersions of finely divided solids in hydrophobic, electrically non-conductive oils wherein the viscosity of the fluid increases rapidly and reversibly from a low viscosity fluid to a highly viscous, plastic or solid state under the imposition of a sufficiently powerful electric field. Usually the increase in viscosity of the electro-viscous fluid is proportional to the applied voltage. The materials respond both to direct and alternating current, but it is required that there be very little flow of current through the electro-viscous fluid. These fluids are useful for the transmission of large forces while requiring only a very small amount of electric power. Devices employing electro-viscous fluids include among others clutches, hydraulic valves, shock absorbers, vibrators or devices for positioning and fixing workpieces, computer output devices that create a voltage dependent resistance such as used in virtual reality simulations (e.g. virtual reality simulations of medical surgery), and computer output devices that simulate a surface having a controllable texture such as a refreshable touch pad for reading Braille text.

The non-aqueous liquids useful as a dispersion medium for electro-viscous fluids may be, for example, hydrocarbons such as paraffins, olefins and aromatic hydrocarbons, Silicone oils such as polydimethylsiloxanes and liquid methyl phenyl siloxanes are also used. These may be used singly or as combinations of two or more types. The liquid dispersing medium is selected or formulated so that it is liquid over a fairly wide temperature ranges, usually at least $-30°$ C. ($243°$ K) to $150°$ C. ($423°$ K). The viscosity of the dispersing medium is selected to be as low as praticable without excessive volatility because this enables a lower basic viscosity of the electro-viscous fluid. To avoid sedimentation of the dispersed phase, the dispersing medium and the dispersant should have a density that is approximately equal to each other. When this condition is not fulfilled either the dispersant floats to the surface of the fluid because it is less dense or it settles to the bottom of the fluid because it is more dense.

In many known electro-viscous fluids the disperse phase consists of inorganic solids such as silica gel, zeolites, alumina, titania, spherical particles obtained by the hydrolysis and condensation of metal alkoxides, polymers, substituted silicone resins and composite particles obtained by the condensation of ionic polymers with certain silicon compounds. In general, the effects of an electric field dependent viscosity is believed to be due to the presence of adsorbed water on the particles of the dispersed phase. Ions present in the adsorbed water thus align with the field and thus the particles repel one another with a force proportional to the applied electric field.

In addition to the density considerations required for the disperse phase of an electro-viscous material the particle size and the particle size distribution have an effect on the electro-viscous effect. Generally particles having an average particle diameter of from 0.2 to 30 micrometers and a particle distribution relative half-width value below 0.8. The relative half width value is usually defined to be the absolute half-width value of the distribution divided by the average particle diameter.

SUMMARY OF THE INVENTION

The present invention provides for a polyfluoroalkyl silicone having the general formula:

$M_a M'_b D_c D'_d T_e T'_f Q_g$;

where $M = R^1_u R^2_v R^3_w SiO_{1/2}$ with the sum of the subscripts u+v+w being 3 and the subscripts v and w are each independently 0 or 1;

$M' = R^4 R^5 R^6 SiO_{1/2}$;

$D = R^7_x R^8_y SiO_{2/2}$ with the sum of the subscripts x+y being 2 and y is 0 or 1;

$D' = R^9 R^{10} SiO_{2/2}$;

$T = R^{11}_z SiO_{3/2}$ with the subscript z being 1;

$T' = R^{12} SiO_{3/2}$; and $Q = SiO_{4/2}$;

where the substituent groups $R^2$, $R^3$, $R^4$, $R^5$, $R^6$, $R^8$, $R^9$, $R^{10}$, and $R^{12}$ are each independently selected from the group of one to forty carbon atom monovalent hydrocarbon radicals, the subscripts a, b, c, d, e, f, and g are zero or positive integers with the substituent groups, $R^1$, $R^7$, and $R^{11}$, each independently selected from the group of consisting of monovalent polyfluoroalkyl groups having the formula $CF_3(CF_2)_n(CH_2)_m$ and monovalent polyfluoroalkyl groups having the formula $CF_3(CF_2)_n J(CH_2)_m$ where the subscript n is an integer that ranges from about 3 to about 20, the subscript m is an integer that ranges from about 2 to about 20, J is a divalent methylene group ($CH_2$), divalent sulfur (S), or oxygen (O); subject to the following limitations on the stoichiometric subscripts a, b, c, and e:

1) $a+b \geq 2$;
2) $a+c+e \geq 1$; and
3) $a(u)+c(x)+e(z) \geq 2$.

The present invention further provides for an electro-viscous fluid comprising:

a) a polyfluoroalkyl silicone as previously described b) an electro-active material wherein the density of the electro-active material is approximately equal to the density of the polyfluoroalkyl silicone.

The electro-active materials particularly useful in the practice of the present invention are selected from the group consisting of:

silica gel, zeolites, alumina, titania, spherical particles obtained by the hydrolysis and condensation of metal alkoxides, polymers, substituted silicone resins and composite particles obtained by the condensation of ionic polymers with certain silicon compounds. Particularly preferred polyfluoroalkyl silicones are those wherein the polyfluoroalkyl silicone has a value for the subscript n of 3 and a value of the subscript m of 2. Other preferred electro-viscous materials are those wherein the polyfluoroalkyl silicone is a copolymer wherein $c+d \geq 2$.

DETAILED DESCRIPTION OF THE INVENTION

The present invention relates to a new composition of matter relating to siloxane compounds that have been substituted with two or more polyfluoroalkyl groups suitable for applications involving electro-viscosity, a process for their preparation and methods of use. The compounds or molecules of the present invention are hydrophobic fluid dispersing agents for an electro-active particulate dispersant (electro-active material) having a density approximately equal to the density of the dispersing fluid. By approximately equal applicants define 100±25% as approximately equal. These compounds have the general formula:

$M_a M'_b D_c D'_d T_e T'_f Q_g$;

where $M = R^1_u R^2_v R^3_w SiO_{1/2}$ where the sum of the subscripts $u+v+w$ being 3 and the subscripts v and w are each independently 0 or 1;

$M' = R^4 R^5 R^6 SiO_{1/2}$;

$D = R^7_x R^8_y SiO_{2/2}$ where the sum of the subscripts $x+y$ being 2 and y is 0 or 1;

$D' = R^9 R^{10} SiO_{2/2}$;

$T = R^{11}_z SiO_{3/2}$ where the subscript z being 1;

$T' = R^{12} SiO_{3/2}$; and $Q = SiO_{4/2}$;

where the substituent groups, $R^1$, $R^7$, and $R^{11}$ are each independently selected from the group of consisting of monovalent polyfluoroalkyl groups having the formula:

$CF_3(CF_2)_n(CH_2)_m$ and monovalent polyfluoroalkyl groups having the formula:

$CF_3(CF_2)_n J(CH_2)m$;

the substituent groups $R^2$, $R^3$, $R^4$, $R^5$, $R^6$, $R^8$, $R^9$, $R^{10}$, and $R^{12}$ are each independently selected from the group of one to forty carbon atom monovalent hydrocarbon radicals, where the subscripts a, b, c, d, e, f, and g are zero or positive integers, where the subscript n is an integer that ranges from about 3 to about 20, preferably from about 4 to about 19, more preferably from about 4 to about 18 and most preferably from about 6 to about 18, where the subscript m is an integer that ranges from about 2 to about 20, preferably from about 2 to about 10, more preferably from about 2 to 8 and most preferably from about 4 to 6, J is a divalent methylene group ($CH_2$), divalent sulfur (S), or oxygen (O); subject to the following limitations on the stoichiometric subscripts: $a+b \geq 2$, the sum of the subscripts a and b is equal to or greater than 2; $a+c+e \geq 1$, the sum of the subscripts a, c, and e is equal to or greater than one; and $a(u)+c(x)+e(z) \geq 2$, the sum of the products of the subscripts a times u, c times x and e times z is greater than or equal to 2. The sum of the products limitation requires at least two polyfluoroalkyl groups per polyfluoroalkyl silicone. It is preferred that there be at least three polyfluoroalkyl substituents in the molecule, i.e. $a(u)+c(x)+e(z) \geq 3$, it is more preferred that there be at least four polyfluoroalkyl substituents in the molecule, i.e. $a(u)+c(x)+e(z) \geq 4$, and it is most preferred that there be at least five polyfluoroalkyl substituents in the molecule, i.e. $a(u)+c(x)+e(z) \geq 5$. Preferably compounds of the present invention have a viscosity ranging from about 5 to about 40 centipoise at 25° C., preferably ranging from about 8 to about 35 centipoise at 25° C., more preferably ranging from about 10 to about 30 centipoise at 25° C., and most preferably ranging from about 12 to about 30 centipoise at 25° C.

In the absence of an electric field, the electro-viscous fluids made possible by the compounds of the present invention should have a viscosity ranging from about 5 to about 40 centipoise at 25° C., preferably ranging from about 8 to about 35 centipoise at 25° C., more preferably ranging from about 10 to about 30 centipoise at 25° C., and most preferably ranging from about 12 to about 30 centipoise at 25° C.

Thus the compounds of the present invention admit a variety of linear and branched siloxane structures, including but not limited to: MM, MM', MDM, MDD'M, MDM', MDD'M', MD'M, MD'M', MT, MT', MDT, M'DT, M'D'T, MM'DD'T, MM'DD'TT', MDTQ, MM'DTQ, MDD'TQ, MM'DD'TT'Q and other various permutations. While not expressly admitting the possibility of three or more M, D, or T groups in any of the foregoing, it is contemplated that M", D", and T" and additional higher order homologues could be included in the general formula to achieve structures of any desired level of complexity. Since some of the subscripts may be zero or positive integers these requirements allow for any geometrical configuration of M, D and T groups that satisfies this threshold. Because of the requirement that the viscosity be low, the preference for increasing numbers of the polyfluoroalkyl substituent in the molecules of the present invention creates competing criteria which produce results opposed to one another, i.e. while the electrorheological properties of the fluid may be improved by increasing the number of polyfluoroalkyl groups, the viscosity increases, which as it increases renders the fluid less satisfactory as an electrorheological fluid. Thus it is necessary to balance the number of polyfluoroalkyl groups against the desired viscosity of the fluid dispersing agent. In order to satisfy the viscosity requirement the subscripts c, d, e, f, and g may be required to be zero, either singly or in any combination. When c, d, e, f, and g are all zero a simple MM or MM' type compound results. When d, e, f, and g are zero an MDM or MDM' type compound results. When e, f, and g are zero an MDD'M, M'DD'M' or MDD'M' type compound results.

The compounds of the present invention are prepared by the process of reacting $CF_3(CF_2)_n(CH_2)_{m-2}CH=CH_2$ or $CF_3(CF_2)_n J(CH_2)_{m-2}CH=CH_2$ with an alkyl-dihalo-silane, e.g. $(CH_3)Cl_2Si-H$, or a di-alkyl-halo-silane, e.g. $(CH_3)_2 ClSi-H$, under hydrosilylation conditions in the presence of a known Pt hydrosilylation catalyst either neat or in a hydrocarbon solvent. While it is possible to utilize other hydride sources for the hydrosilylation reaction, e.g. methylhydrogen siloxanes, these materials generally do not yield the desired alpha-addition product. Instead these materials yield an undesired mixture of the alpha and beta adducts. When the beta adduct results, elimination of silylfluoride species occurs accompanied by an isomerization to an internal olefin that is unreactive. In order to achieve the desired hydrosilylation adduct, the polyfluoroalkyl group must have the strongly inductive effect of the fluorine mitigated by an interposed methylene group, divalent sulfur or divalent oxygen species.

The resulting polyfluoroalkylhalosilane is a precursor to the compounds of the present invention by reaction pathways and synthetic pathways known in the art. In one instance, the resulting polyfluoroalkylhalosilane is reacted with sodium bicarbonate in anhydrous acetone to yield the coupled product having the general formula, MM.

In general any electro-active material (electro-active dispersant) having approximately the same density as the suspending fluid will provide an electro-viscous fluid. Thus electro-active materials having densities approximately equal to that of the polyfluoroalkyl silicone may be dispersed in the polyfluoroalkyl silicone thereby forming an electro-viscous fluid. Some of the electro-active materials useful in formulating the electro-active fluids comprising a polyfluoroalkyl silicone of the present invention are inorganic solids such as silica gel, zeolites, alumina, titania, spherical particles obtained by the hydrolysis and condensation of metal alkoxides, polymers, substituted silicone resins and composite particles obtained by the condensation of ionic polymers with certain silicon compounds. The term electro-viscous as applied to a fluid means a fluid that exhibits a measurably different viscosity in the presence of an applied electric field in comparison to the viscosity in the absence of an applied electric field. The term electro-active material or dispersant as used herein means a material which when dispersed in a fluid renders the fluid electro-viscous.

In addition to the density considerations required for the disperse phase of an electro-viscous material the particle size and the particle size distribution have an effect on the electro-viscous effect. Generally particles having an average particle diameter of from about 0.2 to about 30 micrometers and a particle distribution relative half-width value below 0.8. The relative half width value is usually defined to be the absolute half-width value of the distribution divided by the average particle diameter.

EXPERIMENTAL

Brookfield viscosity measurements were made using a Brookfield digital viscosimeter, model DV-2 at 20 rpm using a no. 2 spindle.

Preparation of 1H, 1H, 2H, 2H-perfluoroalkyldimethylchlorosilane

A 316 stainless steel Parr rocking bomb shaker was charged with 450 g of DuPont BL fluorinated telomeric olefin, a mixture of compounds having the formula $CF_3(CF_2)_nCH=CH_2$ with an average molecular weight of approximately 421, 105 g of dimethylchlorosilane and 0.067 g of a platinum catalyst derived from chloroplatinic acid (Karstedt type). The air in the reaction vessel was displaced with nitrogen and the reaction vessel was sealed. The vessel was heated to 80° C. and agitated at 80° C. for approximately 12 hours. As the reaction proceeded a pressure decrease was observed and when there was no further decrease in pressure the reaction was considered complete. After cooling the reaction vessel, the contents were discharged and unreacted dimethylchlorosilane was removed from the reaction mixture by distillation. The residue remaining, the product, was treated with 4.0 g of activated charcoal and stirred for one hour followed by filtration through Celite 545™ to yield 474 g of clear fluid having a specific gravity of 1.5582 at 23° C.

Preparation of 1,3-bis(1H, 1H, 2H, 2H-perfluoroalkyl)-1,1,3,3-tetramethyldisiloxane A 5 liter vessel was charged with 500 g of acetone and 43.2 g of anhydrous sodium bicarbonate. 500 g of 1H, 1H, 2H, 2H-perfluoroalkyldimethylchlorosilane was added to the acetone sodium bicarbonate mixture slowly over a period of 3 to 3.5 hours at a temperature of 23 to 24° C. The reaction mixture was heated to reflux and refluxed two hours at 67° C. The reaction mixture was then cooled to room temperature and filtered through Celite 545™ to remove salts produced by the reaction and unreacted sodium bicarbonate. The resulting liquid product was washed with de-ionized water until the material was free of dissolved HCl. The liquid was then stripped of low boiling components and then was vacuum distilled at a temperature of 180–185° C. at 30 mm Hg. The resulting product was treated with activated charcoal and filtered through Celite 545™ to provide 335 g of a clear colorless fluid having a specific gravity of 1.5137 at 25° C., a refractive index of 1.3369 at 24.8° C. and a Brookfield viscosity of 24 cps. At 25° C. Fourier transform infrared spectroscopy (FTIR) and proton nuclear magnetic resonance ($^1H$ nmr) are consistent with the structure of 1,3-bis(1H, 1H, 2H, 2H-perfluoroalkyl)-1,1,3,3-tetramethyldisiloxane.

Preparation of 1H, 1H, 2H, 2H-nonafluorohexyldimethylchlorosilane

A 316 stainless steel Parr rocking bomb shaker was charged with 389.3 g of 3,3,4,4,5,5,6,6,6-nonafluorohexene-1, 150 g of dimethylchlorosilane and 70 micro liters of a 5.1 wt. % platinum catalyst solution derived from chloroplatinic acid (Karstedt type). The air in the reaction vessel was displaced with nitrogen and the reaction vessel was sealed. The vessel was heated to 80° C. and agitated at 80° C. for approximately 12 hours. As the reaction proceeded a pressure decrease was observed and when there was no further decrease in pressure the reaction was considered complete. After cooling the reaction vessel, the contents were discharged and unreacted dimethylchlorosilane was removed from the reaction mixture by distillation. The residue remaining, the product, was treated with 3.0 g of activated charcoal and stirred for one hour followed by filtration through Celite 545™ to yield 350 g of clear fluid having a specific gravity of 1.3447 at 25° C. Structure of the compound was confirmed by FTIR and $^1H$ nmr.

Preparation of 1-(1H, 1H, 2H, 2H-perfluoroalkyl)-3- (1H, 1H, 2H, 2H -3,3,4,4,5,5,6,6,6-nonafluorohexyl)-1,1,3,3-tetramethyldisiloxane A 3 liter vessel was charged with 800 mL of acetone and 81.2 g of anhydrous sodium bicarbonate. 500 g of 1H, 1H, 2H, 2H-perfluoroalkyldimethylchlorosilane and 330 g of 1H, 1H, 2H, 2H-nonafluorohexyldimethylchlorosilane was added to the acetone sodium bicarbonate mixture slowly over a period of 2 hours at a temperature of 24° C. The reaction mixture was heated to reflux and refluxed two hours at 68° C. The reaction mixture was then cooled to room temperature and filtered through Celite 545™ to remove salts produced by the reaction and unreacted sodium bicarbonate. The resulting liquid product was washed with deionized water until the material was free of dissolved HCl. The liquid was then stripped of low boiling components and then was vacuum distilled at a head temperature of 95° C. at 40 mm Hg. The resulting product was treated with activated charcoal and filtered through Celite 545™ to provide 690 g of a clear colorless fluid having a specific gravity of 1.45 at 24° C., a refractive index of 1.3385 at 23.5° C. and a Brookfield viscosity of 25 cps at 25° C. Fourier transform infrared spectroscopy (FTIR) and proton nuclear magnetic resonance ($^1H$ nmr) are consistent with the structure of 1-(1H, 1H, 2H, 2H-perfluoroalkyl)-3-(1H, 1H, 2H, 2H -3,3,4,4,5,5,6,6,6-nonafluorohexyl)-1,1,3,3-tetramethyldisiloxane.

Preparation of 1H, 1H, 2H, 2H-3,3,4,4,5,5,6,6,6-nonafluorohexylmethyldichlorosilane A 5 liter reaction vessel was charged with 500 mL of n-hexane, 403 g of methylchlorosilane and 0.5 mL of a 5.1 wt. % platinum catalyst solution derived from chloroplatinic acid (Karstedt type). The air in the reaction vessel was displaced and blanketed with nitrogen and heated to 31° C. followed by the addition of 755 g of 3,3,4,4,5,5,6,6,6-nonafluorohexene. The vessel was heated to 84° C. for approximately 3 hours. After cooling the reaction vessel, the contents were discharged and unreacted methylchlorosilane was removed from the reaction mixture by distillation. The residue remaining, the product, was treated with 2.0 g of activated charcoal and stirred for one hour followed by filtration through Celite 545™ to yield 836 g of clear fluid. Structure of the compound was confirmed by FTIR and $^1$H nmr.

Co-Hydrolysis of 1H, 1H, 2H, 2H-3,3,4,4,5,5,6,6,6-nonafluorohexylmethyldichlorosilane and 3,3,3-trifluoropropylmethyldichlorosilane 1.850 L of distilled water and 1.127 L (1.0143 kg) of concentrated ammonium hydroxide (29.0 wt. % $NH_4OH$) was added to a 5 L flask. A mixture of 460.0 g of 1H, 1H, 2H, 2H-3,3,4,4,5,5,6,6,6-nonafluorohexylmethyldichlorosilane and 542.1 g of 3,3,3-trifluoropropyl-methyldichlorosilane was prepared. The mixture of the two dichlorosilane compounds was introduced slowly into the 5 L flask below the surface of the liquid over a period of 2 hours and the mixture was then stirred for an additional two hours. After stirring was completed, the reaction mixture was allowed to separate into two phases and the product phase was washed with de-ionized water until it was free of detectable base. The resulting clear colorless fluid was dried over silica gel to provide 693.0 g of product having a Brookfield viscosity of 150 cps at 25° C., a refractive index of 1.3628 at 25° C. and a specific gravity of 1.3918 at 25° C. The FTIR and $^{29}$Si nmr are in agreement with a polysiloxane structure that possesses both the nonafluorohexyl moiety and the trifluoropropyl moiety.

Preparation of a Copolymer Containing 1H, 1H, 2H, 2H-3,3,4,4,5,5,6,6,6-nonafluorohexylsiloxyl D units and 3,3,3-trifluoropropylsiloxyl D units endcapped with Trimethylsilyl Groups To 600 grams of the co-hydrolysis product of the mixture of 1H, 1H, 2H, 2H-3,3,4,4,5,5,6,6,6-nonafluorohexylmethyldichlorosilane and 3,3,3-trifluoropropyl-methyldichlorosilane was added 93.0 g (120 mL) of hexamethyldisilazane under a blanket of nitrogen in an appropriate reaction vessel. After addition of the hexamethyldisilazane was completed, the contents of the reaction vessel were heated to 80° C. for a period of two hours. The reaction mixture was then allowed to cool to room temperature under a nitrogen blanket followed by application of a nitrogen sparge under a vacuum of 20 mm Hg while heating to 160° C. which removed volatiles and unreacted hexamethyldisilazane, yielding 721.02 g of a clear colorless liquid having a viscosity of 22.7 cSt at 25° C., a refractive index of 1.3573 at 23.8° C. and a specific gravity of 1.3175 at 25° C. The FTIR and $^{29}$Si nmr are in agreement with a copolymeric polysiloxane structure that possesses both the nonafluorohexyl moiety and the trifluoropropyl moiety endcapped with trimethylsilyl groups. For a copolymer the additional stoichiometric condition on the subscripts is that $c+d \geq 2$.

We claim:

1. An electro-viscous fluid comprising:

the polyfluoroalkyl silicone having the general formula:

where $M = R^1{}_u R^2{}_v R^3{}_w SiO_{1/2}$ with the sum of the subscripts $u+v+w$ being 3 and the subscripts v and w are each independently 0 or 1;

$M' = R^4 R^5 R^6 SiO_{1/2}$;

$D = R^7{}_x R^8{}_y SiO_{2/2}$ with the sum of the subscripts $x+y$ being 2 and y is 0 or 1;

$D' = R^9 R^{10} SiO_{2/2}$;

$T = R^{11}{}_z SiO_{3/2}$ with the subscript z being 1;

$T' = R^{12} SiO_{3/2}$; and $Q = SiO_{4/2}$;

where the substituent groups $R^2$, $R^3$, $R^4$, $R^5$, $R^6$, $R^8$, $R^9$, $R^{10}$, and $R^{12}$ are each independently selected from the group of one to forty carbon atom monovalent hydrocarbon radicals, the subscripts a, b, c, d, e, f, and g are zero or positive integers with the substituent groups, $R^1$, $R^7$, and $R^{11}$, each independently selected from the group of consisting of monovalent polyfluoroalkyl groups having the formula $CF_3(CF_2)_n(CH_2)_m$ and monovalent polyfluoroalkyl groups having the formula $CF_3(CF_2)_n J(CH_2)_m$ where the subscript n is an integer that ranges from about 3 to about 20, the subscript m is an integer that ranges from about 2 to about 20, J is a divalent methylene group ($CH_2$), divalent suilfuir (S), or oxygen (O); subject to the following limitations on the stoichiometric subscripts a, b, c, and e:

1) $a+b>2, a+c+e>1$; and
2) $a(u)+c(x)+e(z)>2$ and
   b) an electro-active material wherein the density of the electro-active material is approximately equal to the density of the polyfluoroalkyl silicone.

2. The electro-viscous material of claim 1 where the electro-active material is selected from the group consisting of:

silica gel, zeolites, alumina, titania, spherical particles obtained by the hydrolysis and condensation of metal alkoxides, polymers, substituted silicone resins and composite particles obtained by the condensation of ionic polymers with certain silicon compounds.

3. The electro-viscous material of claim 2 wherein the polyfluoroalkyl silicone has a value for the subscript n of 3 and a value of the subscript m of 2.

4. The electro-viscous material of claim 2 wherein the polyfluoroalkyl silicone is a copolymer wherein $c+d \geq 2$.

5. The electro-viscous material of claim 4 wherein the polyfluoroalkyl silicone copolymer comprises 1H, 1H, 2H, 2H-3,3,4,4,5,5,6,6,6-nonafluorohexylsiloxyl D units and 3,3,3-trifluoropropylsiloxyl D units.

6. The electro-viscous material of claim 5 wherein the electro-active material has a particle size ranging from about 0.2 to about 30 micrometers.

7. The electro-viscous material of claim 6 wherein the electro-active material has a particle distribution relative half-width value below 0.8.

8. The electro-viscous material of claim 1 wherein the polyfluoroalkyl silicone is 1-(1H, 1H, 2H, 2H-perfluoroalkyl)-3- (1H, 1H, 2H, 2H -3,3,4,4,5,5,6,6,6-nonafluorohexyl)-1,1,3,3-tetramethyldisiloxane.

9. The electro-viscous material of claim 1 wherein the polyfluoroalkyl silicone is 1,3-bis(1H, 1H, 2H, 2H-perfluoroalkyl)-1,1,3,3-tetramethyldisiloxane.

10. The electro-viscous fluid of claim 2 having a polyfluoroalkyl silicone where $a(u)+c(x)+e(z) \geq 3$.

11. An electro-viscous fluid comprising:

a) the polyfluoroalkyl silicone of claim 10 and
b) an electro-active material wherein the density of the electro-active material is approximately equal to the density of the polyfluoroalkyl silicone.

12. The electro-viscous fluid of claim 2 having a polyfluoroalkyl silicone where $a(u)+c(x)+e(z) \geq 4$.

13. An electro-viscous fluid comprising:
a) the polyfluoroalkyl silicone of claim 12 and
b) an electro-active material wherein the density of the electro-active material is approximately equal to the density of the polyfluoroalkyl silicone.

14. The electro-viscous fluid of claim 2 having a polyfluoroalkyl silicone where $a(u)+c(x)+e(z) \geq 5$.

15. An electro-viscous fluid comprising:
a) the polyfluoroalkyl silicone of claim 14 and an electro-active material wherein the density of the electro-active material is approximately equal to the density of the polyfluoroalkyl silicone.

16. An electro-viscous fluid consisting essentially of:
a) a polyfluoroalkyl silicone having the general formula:

$$M_a M'_b D_c D'_d T_e T'_f Q_g;$$

where $M=R^1{}_u R^2{}_v R^3{}_w SiO_{1/2}$ with the sum of the subscripts u+v+w being 3 and the subscripts v and w are each independently 0 or 1;

$M'=R^4 R^5 R^6 SiO_{1/2}$;

$D=R^7{}_x R^8{}_y SiO_{2/2}$ with the sum of the subscripts x+y being 2 and y is 0 or 1;

$D'=R^9 R^{10} SiO_{2/2}$;

$T=R^{11}{}_z SiO_{3/2}$ with the subscript z being 1;

$T'=R^{12} SiO_{3/2}$; and $Q=SiO_{4/2}$;

where the substituent groups $R^2, R^3, R^4, R^5, R^6, R^8, R^9, R^{10}$, and $R^{12}$ are each independently selected from the group of one to forty carbon atom monovalent hydrocarbon radicals, the subscripts a, b, c, d, e, f, and g are zero or positive integers with the substituent groups, $R^1, R^7,$ and $R^{11}$, each independently selected from the group of consisting of monovalent polyfluoroalkyl groups having the formula $CF_3(CF_2)_n(CH_2)_m$ and monovalent polyfluoroalkyl groups having the formula $CF_3(CF_2)_n J(CH_2)_m$ where the subscript n is an integer that ranges from about 3 to about 20, the subscript m is an integer that ranges from about 2 to about 20, J is a divalent methylene group $(CH_2)$, divalent sulfur (S), or oxygen (O); subject to the following limitations on the stoichiometric subscripts a, b, c, and e:

1) $a+b \geq 2$;
2) $a+c+e \geq 1$; and
3) $a(u)+c(x)+e(z) \geq 2$; and b) an electro-active material wherein the density of the electro-active material is approximately equal to the density of the polyfluoroalkyl silicone.

17. An electro-viscous fluid consisting of:
a) a polyfluoroalkyl silicone having the general formula:

$$M_a M'_b D_c D'_d T_e T'_f Q_g;$$

where $M=R^1{}_u R^2{}_v R^3{}_w SiO_{1/2}$ with the sum of the subscripts u+v+w being 3 and the subscripts v and w are each independently 0 or 1;

$M'=R^4 R^5 R^6 SiO_{1/2}$;

$D=R^7{}_x R^8{}_y SiO_{2/2}$ with the sum of the subscripts x+y being 2 and y is 0 or 1;

$D'=R^9 R^{10} SiO_{2/2}$;

$T=R^{11}{}_z SiO_{3/2}$ with the subscript z being 1;

$T'=R^{12} SiO_{3/2}$; and $Q=SiO_{4/2}$;

where the substituent groups $R^2, R^3, R^4, R^5, R^6, R^8, R^9, R^{10}$, and $R^{12}$ are each independently selected from the group of one to forty carbon atom monovalent hydrocarbon radicals, the subscripts a, b, c, d, e, f, and g are zero or positive integers with the substituent groups, $R^1, R^7,$ and $R^{11}$, each independently selected from the group of consisting of monovalent polyfluoroalkyl groups having the formula $CF_3(CF_2)_n(CH_2)_m$ and monovalent polyfluoroalkyl groups having the formula $CF_3(CF_2)_n J(CH_2)_m$ where the subscript n is an integer that ranges from about 3 to about 20, the subscript m is an integer that ranges from about 2 to about 20, J is a divalent methylene group $(CH_2)$, divalent sulfur (S), or oxygen (O); subject to the following limitations on the stoichiometric subscripts a, b, c, and e:

1) $a+b \geq 2$;
2) $a+c+e \geq 1$; and
3) $a(u)+c(x)+e(z) \geq 2$; and b) an electro-active material wherein the density of the electro-active material is approximately equal to the density of the polyfluoroalkyl silicone.

* * * * *